(12) United States Patent
Sheikholeslami et al.

(10) Patent No.: US 10,731,211 B2
(45) Date of Patent: Aug. 4, 2020

(54) METHODS AND COMPOSITIONS FOR LOADING OF POLYMERASE COMPLEXES

(71) Applicant: Pacific Biosciences of California, Inc., Menlo Park, CA (US)

(72) Inventors: Sassan Sheikholeslami, San Francisco, CA (US); Michael Hunkapiller, San Carlos, CA (US); Natasha Popovich, Menlo Park, CA (US); Lei Sun, San Jose, CA (US); Erik Miller, San Francisco, CA (US); Satwik Kamtekar, Redwood City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 410 days.

(21) Appl. No.: 15/354,803

(22) Filed: Nov. 17, 2016

(65) Prior Publication Data
US 2017/0159119 A1 Jun. 8, 2017

Related U.S. Application Data

(60) Provisional application No. 62/257,152, filed on Nov. 18, 2015.

(51) Int. Cl.
  C12Q 1/68 (2018.01)
  C12Q 1/6874 (2018.01)
  C12Q 1/6844 (2018.01)
  C12N 11/02 (2006.01)

(52) U.S. Cl.
  CPC ............ *C12Q 1/6874* (2013.01); *C12N 11/02* (2013.01); *C12Q 1/6846* (2013.01)

(58) Field of Classification Search
  None
  See application file for complete search history.

(56) References Cited

U.S. PATENT DOCUMENTS

| | | |
|---|---|---|
| 4,711,955 A | 12/1987 | Ward et al. |
| 5,143,854 A | 9/1992 | Pirrung et al. |
| 5,328,824 A | 7/1994 | Ward et al. |
| 5,424,186 A | 6/1995 | Fodor et al. |
| 5,476,928 A | 12/1995 | Ward et al. |
| 5,624,711 A | 4/1997 | Sundberg et al. |
| 5,723,584 A | 3/1998 | Schatz |
| 5,874,239 A | 2/1999 | Schatz |
| 5,919,523 A | 7/1999 | Sundberg et al. |
| 5,932,433 A | 8/1999 | Schatz |
| 6,210,891 B1 | 4/2001 | Gupte et al. |
| 6,255,083 B1 | 7/2001 | Williams |
| 6,258,568 B1 | 7/2001 | Nyren |
| 6,265,552 B1 | 7/2001 | Schatz |
| 6,787,308 B2 | 9/2004 | Balasubramanian et al. |
| 6,917,726 B2 | 7/2005 | Levene et al. |
| 7,013,054 B2 | 3/2006 | Levene et al. |
| 7,056,661 B2 | 6/2006 | Korlach et al. |
| 7,057,026 B2 | 6/2006 | Barnes et al. |
| 7,170,050 B2 | 1/2007 | Turner et al. |
| 7,302,146 B2 | 11/2007 | Turner et al. |
| 7,315,019 B2 | 1/2008 | Turner et al. |
| 7,486,865 B2 | 2/2009 | Foquet et al. |
| 7,763,423 B2 | 7/2010 | Roitman et al. |
| 7,767,394 B2 | 8/2010 | Turner et al. |
| 7,820,983 B2 | 10/2010 | Lundquist et al. |
| 7,907,800 B2 | 3/2011 | Foquet et al. |
| 7,931,867 B2 | 4/2011 | Korlach |
| 7,932,035 B2 | 4/2011 | Korlach |
| 7,935,310 B2 | 5/2011 | Korlach |
| 7,993,891 B2 | 8/2011 | Roitman et al. |
| 8,003,330 B2 | 8/2011 | Heiner et al. |
| 8,133,672 B2 | 3/2012 | Bjornson et al. |
| 8,137,942 B2 | 3/2012 | Roitman et al. |
| 8,153,375 B2 | 4/2012 | Travers et al. |
| 8,193,123 B2 | 6/2012 | Rank et al. |
| 8,802,600 B2 | 8/2014 | Rank et al. |
| 8,906,660 B2 | 12/2014 | Kamtekar et al. |
| 8,906,670 B2 | 12/2014 | Gray et al. |
| 8,993,307 B2 | 3/2015 | Zaccarin et al. |
| 8,994,946 B2 | 3/2015 | McCaffrey et al. |
| 9,062,091 B2 | 6/2015 | Bjornson et al. |
| 9,116,118 B2 | 8/2015 | Turner et al. |
| 9,372,308 B1 | 6/2016 | Saxena et al. |
| 2003/0124576 A1 | 7/2003 | Kumar et al. |
| 2004/0241716 A1 | 12/2004 | Kumar et al. |

(Continued)

FOREIGN PATENT DOCUMENTS

| | | |
|---|---|---|
| EP | 1963530 B1 | 7/2011 |
| WO | WO 99/005315 A2 | 2/1999 |

(Continued)

OTHER PUBLICATIONS

Aoki, "Microwell Cluster for Processing Electron Microscope Sections for Immunocytochemistry", Biotech. Histochem. V. 67, n. 2, p. 98-99 (1992).

Beier, et al., "Versatile Derivatisation of Solid Support Media for Covalent bonding on DNA-Microchips", Nucleic Acids Res. v. 27, n. 9, p. 1970-1977 (1999).

Burgers et al. (2001) "Eukaryotic DNA polymerases: proposal for a revised nomenclature" J Biol Chem. 276(47):43487-90.

Clackson et al. (1991) "Making antibody fragments using phage display libraries" Nature 352:624-628.

(Continued)

*Primary Examiner* — Kenneth R Horlick

(74) *Attorney, Agent, or Firm* — Monicia Elrod-Erickson

(57) ABSTRACT

The present disclosure provides methods, compositions, and systems for distributing polymerase compositions into array regions. In particular, the described methods, compositions, and systems utilize density differentials and/or additives to increase efficiency in the distribution of polymerase compositions to a surface as compared to methods utilizing only diffusion control.

29 Claims, 7 Drawing Sheets

(56) References Cited

U.S. PATENT DOCUMENTS

| | | |
|---|---|---|
| 2007/0036511 A1 | 2/2007 | Lundquist et al. |
| 2007/0188750 A1 | 8/2007 | Lundquist et al. |
| 2007/0206187 A1 | 9/2007 | Lundquist et al. |
| 2008/0030628 A1 | 2/2008 | Lundquist et al. |
| 2008/0108082 A1 | 5/2008 | Rank et al. |
| 2009/0029385 A1 | 1/2009 | Christians et al. |
| 2009/0118129 A1 | 5/2009 | Turner |
| 2009/0208961 A1 | 8/2009 | Bjornson et al. |
| 2009/0233302 A1 | 9/2009 | Wegener et al. |
| 2009/0298075 A1 | 12/2009 | Travers et al. |
| 2010/0009872 A1* | 1/2010 | Eid .............. G01N 33/54313 506/26 |
| 2010/0035269 A1 | 2/2010 | Ma et al. |
| 2010/0075332 A1 | 3/2010 | Patel et al. |
| 2010/0093555 A1 | 4/2010 | Bjornson et al. |
| 2010/0099100 A1 | 4/2010 | Zaccarin et al. |
| 2010/0112645 A1 | 5/2010 | Clark et al. |
| 2010/0221716 A1 | 9/2010 | Flusberg et al. |
| 2010/0279283 A1* | 11/2010 | Raghunath .......... C12Q 1/6806 435/6.12 |
| 2011/0059505 A1 | 3/2011 | Hanzel et al. |
| 2011/0117637 A1 | 5/2011 | Gray et al. |
| 2011/0183320 A1 | 7/2011 | Flusberg et al. |
| 2011/0189659 A1 | 8/2011 | Clark et al. |
| 2011/0222179 A1 | 9/2011 | Monadgemi |
| 2011/0256618 A1 | 10/2011 | Eid et al. |
| 2011/0257040 A1 | 10/2011 | Turner et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0034602 A1 | 2/2012 | Emig et al. |
| 2012/0058469 A1 | 3/2012 | Shen |
| 2012/0071359 A1 | 3/2012 | Sun et al. |
| 2012/0085894 A1 | 4/2012 | Zhong et al. |
| 2012/0196279 A1 | 8/2012 | Underwood et al. |
| 2012/0322666 A1 | 12/2012 | Pham et al. |
| 2012/0322692 A1* | 12/2012 | Pham .............. C12Q 1/6869 506/26 |
| 2013/0327644 A1 | 12/2013 | Turner et al. |
| 2014/0051068 A1 | 2/2014 | Cherf et al. |
| 2014/0199016 A1 | 7/2014 | Grot et al. |
| 2014/0287964 A1 | 9/2014 | Lundquist et al. |
| 2015/0065353 A1 | 3/2015 | Turner et al. |
| 2015/0141266 A1 | 5/2015 | Turner et al. |
| 2017/0136433 A1 | 5/2017 | Sun et al. |

FOREIGN PATENT DOCUMENTS

| | | |
|---|---|---|
| WO | WO 07/075987 A2 | 7/2007 |
| WO | WO 07/076057 A2 | 7/2007 |
| WO | WO 07/123763 A2 | 11/2007 |
| WO | WO 08/051530 A2 | 5/2008 |

OTHER PUBLICATIONS

Crameri et al. (1998) "DNA shuffling of a family of genes from diverse species accelerates directed evolution" Nature 391:288-291.

Deng et al., "Prototyping of Masks, Masters and Stamps/Molds for Soft Lithography Using an Office Printer and Photographic Reduction", Anal. Chem. 72:3176-80 (2000).

Driscoll, R. J., et al., Atomic-Scale Imaging of DNA Using Scanning Tunneling Microscopy. Nature, 346(6281): 294-296 (1990).

Eid et al., "Real-Time DNA Sequencing From Single Polymerase Molecules," Science (2009) 323:133-138.

Gibbs et al. (2001) "Degenerate oligonucleotide gene shuffling (DOGS): a method for enhancing the frequency of recombination with family shuffling" Gene 271:13-20.

Goodwin, P. M., et al., Application of Single Molecule Detection to DNA Sequencing. Nucleosides & Nucleotides, 16(5-6): 543-550 (1997).

Hiraga and Arnold (2003) General method for sequence-independent site-directed chimeragenesis: J. Mol. Biol. 330:287-296.

Hong et al., "Self-Assembly of a Dendron Through Multiple Ionic Interaction to Give Mesospacing Between Reactive Amine Groupe on the Surface," Langmuir (2003) 19:2357-2365.

Howorka, S., et al., Sequence-Specific Detection of Individual DNA Strands using Engineered Nanopores, Nature Biotechnology, 19(7): 636-639 (2001).

Hübscher et al. (2002) "Eukaryotic DNA Polymerases" Annual Review of Biochemistry vol. 71: 133-163.

Kane et al., "Patterning Proteins and Cells Using Soft Lithography", Biomaterials. V. 20: p. 2363-76 (1999).

Levene et al., "Zero-mode Waveguides for Single-molecule Analysis at High Concentration" Science (2003) 299:682-686.

Meijer et al. (2001) "Φ29 Family of Phages" Microbiology and Molecular Biology Reviews, 65(2):261-287.

Meller, A., et al., Rapid Nanopore Discrimination Between Single Polynucleotide Molecules, Proceedings of the National Academy of Sciences of the United States of America, 97(3): 1079-1084 (2000).

Rigler, et al., DNA-Sequencing at the Single Molecule Level, Journal of Biotechnology, 86(3): 161 (2001).

Zhu et al., "Analysis of Yeast Protein Kinases Using Protein Chips", Nature Genetics, v. 26, p. 283-289 (2000).

International Search Report, PCT/US2016/062569, dated Mar. 3, 2017.

\* cited by examiner

METHODS AND COMPOSITIONS FOR LOADING OF POLYMERASE COMPLEXES

CROSS REFERENCE TO RELATED APPLICATIONS

The present application claims priority of U.S. Provisional Patent Application No. 62/257,152 filed Nov. 18, 2015, the entire contents of which application is incorporated herein for all purposes by this reference.

BACKGROUND OF THE INVENTION

Techniques in molecular biology and molecular medicine often rely on analysis of single biological molecules. Such techniques include DNA and RNA sequencing, polymorphism detection, the detection of proteins of interest, the detection of protein-nucleic acid complexes, and many others. The high sensitivity, high throughput and low reagent costs involved in single molecule analysis make this type of analysis an increasingly attractive approach for a variety of detection and analysis problems in molecular medicine, from low cost genomics to high sensitivity marker analysis.

For example, single molecule DNA sequencing is useful for the analysis of large sets of related DNAs, such as those that occur in a genome. In some sequencing methods, a polymerase reaction is isolated within an array of extremely small (typically optically confined) observation volumes that permit observation of the enzymatic action of individual polymerases in each reaction/observation volume of the array, while the polymerase copies a template nucleic acid. Nucleotide incorporation events are individually detected, ultimately providing the sequence of the template molecule. This approach dramatically increases throughput of sequencing systems while also dramatically reducing reagent consumption costs, making personalized genomics increasingly feasible.

The small observation volumes often used for single molecule nucleic acid sequencing and other analysis methods are typically provided by immobilizing or otherwise localizing the polymerase (or other) enzyme within a reaction region, which can include an array of extremely smalls wells, such as in an array of Zero Mode Waveguides (ZMWs), and delivering a template, primers, etc., to the wells. One difficulty in performing single molecule analyses occurs in efficiently loading the reaction/observation region of single molecule analysis devices with the molecules of interest (e.g., template or other analyte and/or enzyme or any other associated molecules). Methods of loading that rely on diffusion often require large concentrations of sample in order to load a particular density of reaction regions in a given period of time. It would be desirable to develop methods and compositions for increasing the speed with which molecules are loaded into the reaction/observation regions and thus require lower concentrations of initial sample. Increased efficiency in loading would thus reduce cost and time in terms of sample volumes required and would also simultaneously increase the throughput of such systems. The present disclosure provides these and other features that will be apparent upon complete review of the following.

SUMMARY OF THE INVENTION

Accordingly, the present disclosure provides methods, compositions, and systems for distributing polymerase compositions into array regions. In particular, the methods, compositions, and systems of the present disclosure result in a distribution of polymerase compositions into array regions at a faster rate and/or with less input concentration than is required with typical diffusion loading methods.

In one aspect, the present disclosure provides a method of distributing polymerase molecules into a plurality of array regions, where the method includes the steps of (a) providing a surface comprising a plurality of array regions, wherein the plurality of array regions are bathed in a buffer; (b) exposing the surface to a spike solution comprising polymerase-template complexes, wherein the spike solution has a higher density than the buffer, such that the spike solution sinks to the bottom of the array regions as a thin layer, thereby distributing the polymerase-template complexes into the plurality of the array regions, wherein the distributing occurs at a faster rate as compared to distributing without a spike solution with a higher density than the buffer.

In some embodiments, the spike solution includes a neutral and hydrophilic polysaccharide. In further embodiments, the spike solution includes a volume excluding buffer. In still further embodiments, the spike solution includes an additive selected from the group consisting of dextran, aminodextran, dextrin, cluster dextrin, Ficoll, polyetheylene glycol, sucrose, DMSO, glycerol, and pullulan. In certain embodiments, the spike solution includes Ficoll.

In further embodiments and in accordance with any of the above, the distributing occurs at about a 2 to about a 25-fold, a 5 to about a 20-fold, or about a 10 to about a 15-fold faster rate as compared to distributing without the spike solution. In still further embodiments, the distributing occurs at least 5 times, 10 times, or 15 times faster as compared to distributing without the spike solution.

In any embodiments, the spike solution has a volume that is about 1% to about 20%, 5% to about 15% or 10%-12% of the volume of the buffer.

In some embodiments and in accordance with any of the above, prior exposing step (b), the spike solution is cleaned to remove free polymerases and primers that are not part of polymerase-template complexes from the spike solution. In further embodiments, the spike solution is cleaned by applying a paramagnetic particle to the spike solution to capture free polymerases and templates that are not part of polymerase-template complexes. In still further embodiments, the paramagnetic particle comprises a plurality of oligonucleotides, wherein the oligonucleotides comprise sequences complementary to a primer binding site on the templates.

In some aspects, the present disclosure provides a method of distributing polymerase-template complexes into a plurality of array regions, the method including the steps of (a) providing a surface comprising a plurality of array regions, wherein the plurality of array regions comprise a buffer; (b) forming polymerase-template complexes in a high density spike solution; (c) exposing the high density spike solution to primer complement beads to bind excess polymerases and templates that have not formed into complexes; (d) removing the primer complement beads and any bound polymerases and templates from the solution to produce a cleaned solution; (e) applying the cleaned solution to the plurality of array regions, wherein the cleaned solution has a higher density than the buffer, such that the cleaned solution sinks to the bottom of the array regions, thereby distributing the polymerase-template complexes into the plurality of array regions. In some embodiments, the high density solution comprises a member selected from the group consisting of dextran, aminodextran, dextrin, cluster dextran, Ficoll, polyetheylene glycol, sucrose, DMSO, glycerol, and pullulan.

In some aspects, the present disclosure provides a method of distributing polymerase molecules into a plurality of array regions, the method including the steps of: (a) providing a plurality of array regions, wherein the plurality of array regions is coated with a non-aqueous solution; (b) adding droplets of aqueous solution comprising polymerase molecules to the non-aqueous solution such that the droplets sink through the non-aqueous solution to form a film over the array regions; thereby distributing the polymerase molecules into the plurality of array regions. In certain embodiments, the hydrophobic liquid includes mineral oil.

In some aspects, the methods of the disclosure provided herein include the use of a magnetic particle, where the particle has attached to its surface a plurality of oligonucleotides, wherein the oligonucleotides comprise a spacer and a sequence complementary to a primer.

In some embodiments, the particle is a spherical bead. In further embodiments, the particle is a paramagnetic particle. In still further embodiments, the particle further comprises a polymer layer.

In further embodiments and in accordance with the above, the particle is a bead of about 100 to about 750 nm or 150 to about 650 nm in diameter. In still further embodiments, the particle is a bead of about 500 nm in diameter.

In yet further embodiments and in accordance with any of the above, the spacer is between the bead and the sequence complementary to a primer.

In still further embodiments, the spacer is of sufficient length to stabilize association of a polymerase to the oligonucleotides. In yet further embodiments, the spacer is an oligonucleotide. In further embodiments and in accordance with any of the above, the oligonucleotide has a length of about 10 to about 15 bp.

In yet further embodiments and in accordance with any of the above, the spacer comprises a linker. In still further embodiments, the linker is a member selected from the group consisting of: saccharide, amino acid, substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl.

In some aspects, the present disclosure provides a method of distributing polymerase compositions onto a surface, the method including the steps of: (a) providing a polymerase composition in a solution comprising a carbohydrate additive; (b) adding the solution to the surface; and (c) dehydrating the solution to concentrate the polymerase composition to the surface, thereby distributing the polymerase composition to the surface.

DETAILED DESCRIPTION OF THE INVENTION

Figure 1:
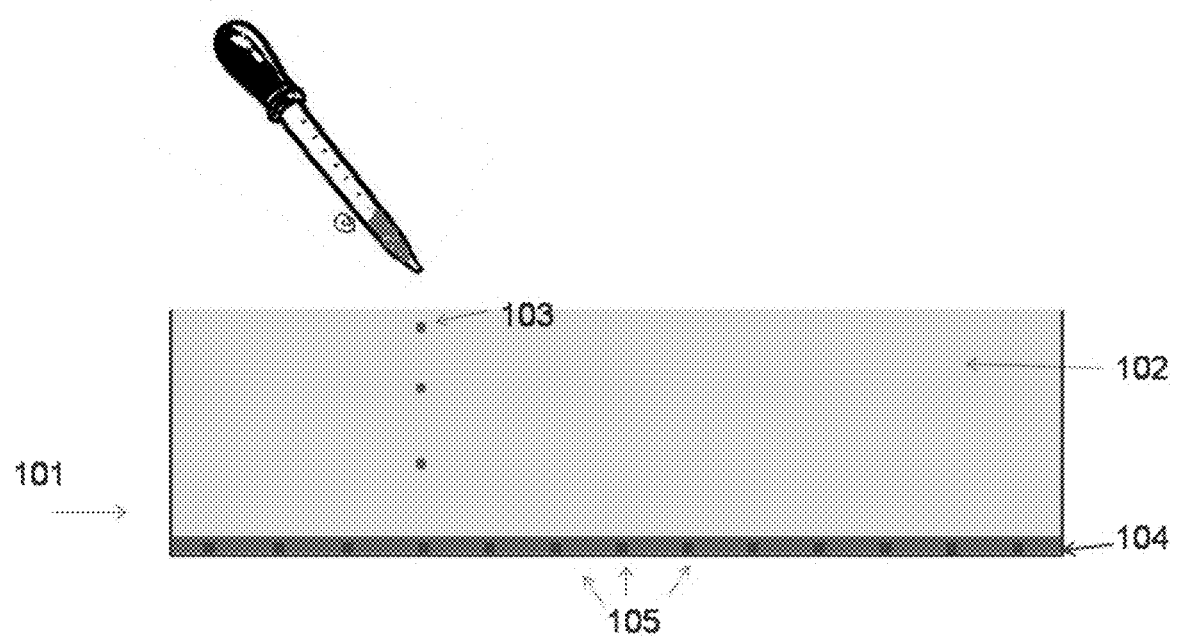
FIG. 1 is a schematic illustration of an embodiment of the invention.

The practice of the inventions described in the present disclosure may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which the disclosed invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

As used herein, a "substantially identical" nucleic acid is one that has at least 80%, 85%, 90%, 95%, 96%, 97%, 98% or 99% A sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

I. Overview

The present disclosure is directed to methods, devices, compositions and systems for distributing enzyme molecules (and any molecules or compounds associated with those enzyme molecules) into a plurality of array regions. In general, the methods, devices, compositions and systems of the present invention result in improved loading of compositions to a surface as compared to typical diffusion loading methods. Note that although for ease of discussion, the majority of the discussion herein is in terms of polymerase enzymes and polymerase compositions, it will be appreciated that any other molecule, including other enzymes or other proteins, molecules, or nucleic acids, can be used in the methods, devices, compositions, and systems of the invention. In other words, any of the loading methods described herein can be used to load nucleic acids alone, enzymes alone, or any combination of enzymes and nucleic acids, including polymerase enzymes complexed with a nucleic acid template. By "polymerase compositions" as used herein is meant to encompass compositions comprising polymerase enzymes as well as any associated molecules, including for example nucleic acid templates and primer sequences. In certain examples, the polymerase compositions comprise polymerase complexes in which a polymerase is attached to a nucleic acid template that is in some examples also further hybridized to a primer.

The methods and systems described herein improve the rate at which nucleic acids and/or polymerase enzymes and any associated molecules are loaded to reaction regions on a surface as compared to typical diffusion methods. Typical diffusion loading methods will rely on diffusion (and gravity) to load molecules to a surface without the use of solutions with density differentials as described herein. As such, typical diffusion loading methods generally require higher concentrations of input sample to load compositions to a surface in a given amount of time. In contrast, the methods and systems described have improved efficiency of loading, such that a smaller input concentration is required to load compositions to a surface in the same given amount of time.

In general, and as is schematically illustrated in FIG. 1, the methods described herein utilize a density differential between the solution bathing the surface and the solution containing the compositions of interest (including nucleic acids and/or polymerase compositions) to increase the efficiency of the loading of those polymerase compositions to the surface. By increasing the efficiency of loading is meant increasing the speed at which the compositions reach the surface and/or decreasing the amount of input concentration needed to occupy by the surface within a given time frame.

As shown in FIG. 1, a surface (101) is covered in a standard buffer (102). In certain non-limiting examples, that surface further includes a plurality of array regions (105). The solution containing the polymerase compositions (103) (also referred to herein as a "spike" solution) has a higher density than the standard buffer (102), and when the higher density spike solution (103) is added to buffer (102) the higher density solution travels through that buffer to cover the surface (104) as well as any array regions (105) on that surface—as a result, the polymerase compositions in that spike solution are also carried to the surface and loaded into the array regions. The density differential allows the spike solution to carry the polymerase compositions to the surface in an efficient manner. This high density loading results in increased speed of loading of the enzyme compositions as compared to method relying on typical diffusion controlled methods.

In further examples, the spike solution includes a monosaccharide or a polysaccharide. In a further example, the spike solution includes a neutral and hydrophilic polysaccharide. In some examples, the spike solution includes a highly branched, high-mass polysaccharide. In further examples, the spike solution includes a volume excluding buffer. In still further examples, the spike solution includes an additive that includes without limitation dextran, amino-dextran, dextrin, cluster dextrin, Ficoll, polyetheylene glycol, sucrose, DMSO, glycerol, and pullulan. In certain examples, the additive used to increase the density of the spike solution is Ficoll. Ficoll is a neutral, highly branched, high-mass, hydrophilic polysaccharide which dissolves readily in aqueous solutions. Ficoll radii range from 2-7 nm. It can be prepared by reaction of a polysaccharide with epichlorohydrin. Pullulan is a polysaccharide polymer typically consisting of maltotriose units, also known as α-1,4-; α-1,6-glucan'. The glucose units in maltotriose are connected by an α-1,4 glycosidic bond, whereas consecutive maltotriose units are connected to each other by an α-1,6 glycosidic bond.

In further examples, it can be desirable to load polymerase compositions that have been enriched for complexes in which a polymerase enzyme is complexed with a nucleic acid template, and that nucleic acid template is further hybridized to a primer (such complexes are also referred to herein as "polymerase complexes" and "polymerase-nucleic acid complexes"). Thus, in one aspect the present disclosure provides a way to enrich the spike solutions for such polymerase complexes that includes a step in which molecules that are not appropriate for loading are removed from the spike solution. For example, in situations in which it is desired to load polymerase complexes, the cleaning step removes "free" polymerase enzymes and primers—i.e., polymerase enzymes and primers that are not part of a polymerase-nucleic acid complex. In certain examples, this cleaning step is accomplished using particles that are able to bind to the non-complexed molecules. Such methods are of particular use in situations where high concentrations of primers and polymerases are used in order to bias complex-formation. An exemplary illustration of such particles is provided in FIG. 2. In this non-limiting example, the particle is a bead (201) that has attached to it a plurality of oligonucleotides (202). Polymerase enzymes and primers that are not part of a complex are able to bind to or otherwise associate with the plurality of oligonucleotides on the bead and can then be removed from the spike solution by removing the particles using any methods known in the art and described herein. In certain examples, the bead is a paramagnetic bead, and removing the bead (and any associated polymerase enzymes, nucleic acid templates, and primers) involves using a magnetic field. In yet further examples, the plurality of oligonucleotides attached to the particles further include a spacer (203). In general, the spacer is of sufficient length that association of polymerases with the oligonucleotides is stabilized as compared to situations in which the spacer is not present or is not of the proper length. The spacer may itself be in certain examples a series of nucleotides or a linker molecule. In examples in which the spacer is a series of nucleotides, the sequence of nucleotides is generally one that will not itself hybridize to a primer or template nucleic acid. Such a sequence produces a distance between the particle and the remainder of the oligonucleotide that stabilizes the association of polymerases as well as nucleic acid templates and primers to the plurality of oligonucleotides attached to the bead. In further examples in which the spacer is a series of nucleotides, the spacer generally has a length of about 10 to about 20 basepairs (bp). For any of the particles that are used in the cleaning step of the loading process, the cleaning step generally involves (i) applying the particles to the spike solution under sufficient time and other conditions to associate with free (e.g., non-complexed) polymerase enzymes and primers, and (ii) removing the particles and their associated molecules to leave a spike solution that is enriched for the complexes of interest. As will be appreciated, the particles can be designed to leave the spike solution enriched for whatever combination of molecules that is required—for example, the particles can be designed to associate with free primers but not with as many polymerases through modifications of the attached oligonucleotides and spacers.

In further examples the spike solutions contain a range of buffer conditions that facilitate the cleaning step discussed above. Such buffer conditions include without limitation the presence of a salt in the concentration of about 150-250 mM. That salt is in further examples a strontium salt. In addition, the buffer conditions may further include dNTPs in a concentration range of about 100-500 µM.

In some examples, polymerase enzymes are loaded onto a surface through the use of immiscible liquids. In such examples, a surface is covered by a nonaqueous solution (in one non-limiting example, mineral oil). Droplets of aqueous solution comprising polymerase molecules (and/or other molecules) are added to the nonaqueous solution such that the aqueous droplets sink through the non-aqueous solution to form a film over the surface.

In some examples, polymerase compositions are loaded onto a surface through an evaporative loading procedure in which the non-volatile components of a solution (e.g., polymerase enzymes and/or other associated molecules, such as nucleic acid templates and primers) are added to a surface in a buffer containing carbohydrate. The buffer is dehydrated, concentrating the polymerase compositions to the surface while retaining activity. Of note is that the presence of carbohydrates in the buffer, including without limitation sucrose, dextrose, trehalose, and Ficoll, can be important for retaining activity of the polymerase compositions after dehydration.

In further examples, the polymerase enzymes and any associated molecules are loaded onto a surface using any of the loading methods described herein, wherein the surface includes a plurality of array regions. These array regions can in still further examples include nanowells. Such nanowells may in further examples include without limitation zero mode waveguides (ZMWs).

As discussed above and in further detail herein, in some examples, compositions disclosed herein include polymerase molecules complexed to a single template nucleic acid molecule. The single template nucleic acid molecule can comprise DNA, RNA, non-natural nucleotides, or a combination thereof. The template nucleic acid may be single stranded or double stranded. In some examples, the template nucleic acid is double stranded with a first end and a second end. In further examples, a first hairpin oligonucleotide connects each strand of the template nucleic acid at the first end, and a second hairpin oligonucleotide connects each strand of the template nucleic acid at the second end. In some examples, the first and second hairpin oligonucleotides are identical (also described herein as symmetrical templates), and in other examples the first and second hairpin oligonucleotides are not the same (also described herein as asymmetrical templates).

Typically, the polymerase-template complexes that are distributed onto the substrate as described herein are subsequently immobilized or bound to the substrate. For example, the polymerase can have a member of a binding pair connected to it which can bind to the other member of the binding pair attached to the substrate. In some cases the binding pair includes biotin and a protein that binds biotin such as avidin or streptavidin. Many types of binding pairs are known in the art. In some cases, an interaction between biotin and a biotin binding protein such as avidin or streptavidin is used. In some cases, an antibody-antigen interaction, for example between digoxigenin and anti-digoxigenin is used. Reactions that form covalent linkages, for example SNAP or Click chemistry can be used to bind the polymerase-nucleic acid complex to the substrate. Oligonucleotide hybridization can also be used for the attachment.

Typically the polymerase enzyme is attached directly to the substrate. In other embodiments, the nucleic acid template complexed with the polymerase is attached to the substrate. Certain embodiments of template immobilization are provided, e.g., in U.S. Pat. No. 8,481,264 which is incorporated herein by reference. One skilled in the art will appreciate that there are many ways of immobilizing nucleic acids and proteins, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art.

The methods and systems described herein offer several advantages over conventional methods and systems for loading molecules onto a surface. For example, for a given amount of time, the methods and systems described herein allow for smaller amounts of input molecule (such as polymerase enzymes) for the same speed of loading. In some examples, the methods and systems described herein results in about a 2× to about 100× faster loading of the polymerase composition as compared to methods and systems based on diffusion loading without the use of solutions with density differentials. A further advantage of the methods and systems described herein is that a smaller input concentration of polymerase compositions is needed to achieve the same speed and level of loading as under typical diffusion loading methods. A yet further advantage of methods described herein is that in general, applying a sample directly to a surface without the use of the solution differentials described herein would result in a patchy, uneven loading, due to (without being limited by mechanism) evaporation of the sample before it has a chance to evenly cover the entire surface. This is particularly true for surface generally used in reactions such as sequencing reactions, which generally may have surface areas of about 20-150 mm$^2$.

The above aspects and further exemplary embodiments are described in further detail in the following discussion.

II. Methods of Loading

The methods and systems described herein provide for the loading of molecules onto a surface. In general, the present methods, devices, compositions and systems result in improved loading of the enzyme compositions as compared to typical diffusion loading methods.

Although the methods described in the following sections are primarily in terms of loading polymerase compositions, it will be appreciated that any of these methods can be used to load any molecules, including any other enzymes instead of or in addition to polymerase enzymes. In particular, any of the methods described herein may also be used to deliver nucleic acids to a surface, and such a surface may include nanoscale wells or nanopores. In addition, "polymerase compositions" may include any combination of polymerase enzymes, nucleic acid templates, primers, dNTPs, and any other additives. In certain non-limiting embodiments, the polymerase compositions that are loaded in accordance with the methods described herein comprise complexes of polymerases attached to nucleic acid templates, with the nucleic acid templates further hybridized to primers.

In some embodiments, the surface to which the polymerase compositions are loaded in accordance with any of the methods described herein has a circular geometry or a rectangular geometry. In embodiments in which the surface comprises nanoscale wells, such as ZMWs, such a surface may further comprise about 120,000 to about 10,000,000 ZMWs. In embodiments in which the surface has a circular geometry, the surface in general comprises about 100,000; 150,000; 200,000; 250,000 ZMWs. In embodiments in which the surface has a rectangular geometry, the surface comprises about 750,000; 1,000,000; 1,500,000 ZMWs. In further embodiments, the surface comprises about 0.5-20, 1-19, 2-18, 3-17, 4-16, 5-15, 6-14, 7-13, 8-12, 9-11 million ZMWs. In other embodiments, such a surface may include nanopores, and any of the loading methods described herein are equally applicable to delivery of nucleic acids of any type or length to a surface comprising nanopores.

In general, the methods of loading described herein result in about a 2× to about 100× faster loading of the polymerase composition as compared to methods and systems based on diffusion loading without the use of solutions with density or other solution differentials. In certain embodiments, the methods of loading result in about a 5-90×, 10-80×, 15-70×, 20-60×, 25-50×, 30-40× faster loading of the polymerase composition as compared to methods and systems based on diffusion loading without the use of solutions with density or other solution differentials.

II.A. Methods Utilizing Spike Solutions

In certain aspects, the methods and systems described herein leverage a density differential between a spike solution and the solution covering a surface to increase the efficiency with which compositions are loaded to the surface.

In specific embodiments, a surface is covered in a standard buffer. In certain non-limiting examples, that surface further includes a plurality of array regions, which may in turn comprise without limitation nanowells (also referred to herein as nanoscale wells) or nanopores. In embodiments involving nanowells, the nanowells may comprise without limitation ZMWs. Regardless of the nature of the surface being loaded, the spike solution containing the polymerase compositions in general has a higher density than the standard buffer covering the surface, such that when the higher density spike solution is added to buffer the higher density solution travels through that buffer to cover the surface as well as any array regions (105) on that surface. As a result, the polymerase compositions in that spike solution are also carried to the surface and loaded into any array regions on that surface. The density differential allows the spike solution to carry the polymerase compositions to the surface in an efficient manner. This high density loading results in increased speed of loading of the enzyme compositions as compared to method relying on typical diffusion controlled methods.

The density of the spike solution can be heightened in comparison to the standard buffer covering the surface using additives known in the art and described herein. In certain exemplary embodiments, the spike solution comprises a neutral and hydrophilic polysaccharide. In further embodiments, the spike solution comprises a highly branched, high-mass polysaccharide. In still further embodiments, the spike solution comprises a volume excluding buffer. In yet further embodiments, the spike solution comprises an additive selected from the group consisting of dextran, aminodextran, dextrin, cluster dextrin, Ficoll, polyetheylene glycol, sucrose, DMSO, glycerol, and pullulan. In particular embodiments, the spike solution comprises Ficoll. Such additives may be included at concentrations of between about 1-20% by volume (v/v). In further embodiments, such additives are included at concentrations of about 2-18%, 5-15%, 8-10% by volume.

As will be appreciated, additives can be included in the solution at any concentration useful for increasing the density of the solution. In certain embodiments, any of the additives discussed above, including without limitation Ficoll, is present in the solution at a concentration range of about 3-10%.

As discussed herein, the loading of the polymerase compositions using the spike solution (also referred to herein as "distributing" the polymerase compositions) occurs about 2-50 fold faster as compared to distributing by diffusion without the spike solution. In further embodiments, the distributing with the spike solution occurs at about a 5-45, 10-40, 15-35, 20-30 fold faster rate as compared to distributing without the spike solution. In still further embodiments, the distributing with the spike solution occurs at least 2, 5, 10, 20, 50, 75, 100, 150, or 200-fold faster as compared to distributing by diffusion without the spike solution.

In further embodiments, the spike solution has a lower volume than that of the buffer bathing the surface onto which the polymerase compositions are to be distributed. In some embodiments, the spike solution has a volume that is about 1% to about 20% of the volume of the buffer. In further embodiments, the spike solution has a volume of about 1-30%, 5-15%, 10-25%, or 15-20% of the volume of the buffer. In yet further embodiments, the spike solution has a volume of about 2%, 5%, 10%, 15%, 20%, 25%, 30%, 35%, 40%, 45%, or 50% of the volume of the buffer. In still further embodiments, the volume of the spike solution is in a ratio to the volume of the buffer of about 1:5, 1:7, 1:9, 1:10, 1:12, 1:15, 1:20, 1:30, 1:40, or 1:50.

In still further embodiments, the above-described loading methods further include a cleaning step to remove molecules from the spike solution. Such a cleaning step is generally used when a specific set of molecules or complexes is desired for loading onto the surface. In some non-limiting examples, spike solutions enriched for polymerase-nucleic acid complexes are desired. In such examples, the cleaning step removes free polymerases, nucleic acid templates and primers that are not part of complexes from the spike solution.

In general, the cleaning step is accomplished by applying particles to the spike solution to capture the molecules that need to be removed. In some embodiments, the particle is a paramagnetic particle that captures free primers, polymerases and polymerase that are bound to primers but are not otherwise part of polymerase-template complexes. In further embodiments, a plurality of oligonucleotides are attached to the paramagnetic particles, and in yet further embodiments, the molecules that are to be removed from the spike solution attach to the oligonucleotides, and the cleaning step further comprises removing the particles and their attached molecules. The attachment of the molecules to be removed can include binding, hybridization, or any other association with the oligonucleotides. As is described in further detail herein, the particles may comprise any number of oligonucleotides. In certain embodiments, the particles comprise about 50,000-100,000 or more oligonucleotides. In further embodiments, there is a spacer between the oligonucleotides and the particle, and that spacer may itself comprise a series of nucleotides or a polymeric linker. In yet further embodiments, the spacer is of sufficient length to stabilize the attachment of molecules to the oligonucleotides, particularly the attachment of free polymerases. Without being bound by mechanism, one possibility is that a length of about 10-15 basepairs between the particle and the oligonucleotide (which in certain examples includes a sequence complementary to a primer) produces an optimal structural distance for a free polymerase to attach to the oligonucleotide with more stability as compared to a situation in which a spacer is not used.

In further embodiments, increasing salt concentrations can further enhance density loading as described herein. In certain embodiments, the salt includes without limitation potassium acetate, sodium acetate, sodium chloride, potassium chloride, or any other salt generally used in buffers solutions. In still further embodiments, the high density loading methods utilize spike solutions comprising about 100-600, 150-550, 200-500, 250-450, 300-400 mM salt.

In some embodiments, and in accordance with any of the above, high density loading methods as described herein include providing a surface comprising an array of nanowells. These nanowells may include in further embodiments ZMWs. The surface with the nanowells further comprises a standard buffer solution, including any standard buffers used for example in sequencing reactions and that are known in the art. In certain embodiments, the standard buffer includes a potassium salt and has a pH in the range of 7-9. In some embodiments, the buffer may include Tris acetate or TrisHCl as exemplary embodiments. A spike solution with a higher density than that of the standard buffer and containing complexes of polymerase enzymes attached to nucleic acid templates that are further hybridized with primers is applied to the standard buffer. The higher density of the spike solution causes it to travel through the standard buffer to the nanowells and load the polymerase complexes into the nanowells at a faster rate compared to that seen when there is no density differential between the loading solution and the standard buffer.

The density of the spike solution can be of any density that is higher than that of the standard buffer. In some non-limiting embodiments, the density of the spike solution is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0× higher than the density of the standard buffer. In further embodiments, the spike solution is about 0.5-3×, 0.6-2.5×, 0.8-2.0×, 1.0-1.5× higher than the density of the standard buffer. In still further embodiments, the density (also referred to as specific gravity) of the spike solution is about 2-20% higher than that of the standard buffer. In yet further embodiments, the density of the spike solution is about 1.5-30, 2-28, 3-26, 4-24, 5-22, 6-20, 7-18, 8-16, 9-14, 10-12% higher than the density of the standard buffer. In still further embodiments, the density of the spike solution is about 1-5, 1.1-1.5, 1.2-2.0, 1.3-2.5, 1.4-3.0, 1.5-3.5, 1.6-4.0, 1.7-4.5, 1.8-5, 1.9-5.5, 2.0-6.0 g/cm$^3$.

In some embodiments, the distributing of the molecules to the surface in any of the methods described herein and in accordance with any of the above is complete in about 0.5 to about 5 hours. In still further embodiments, the distributing is complete in about 1-4.5, 1.5-4, 1-3, and 2-3.5 hours.

In yet further embodiments, the amount of input sample, including any one or combination of input nucleic acid templates, polymerase molecules, and primers, produces the same amount of loading in less time than is seen without the use of a high density spike solution. In other words, for the same given amount of time, less input sample is needed to load the same number of molecules to the surface when using the high density solution methods described herein than when using diffusion controlled methods that do not utilize solutions of differing density.

In still further embodiments, among the molecules that are loaded to the surface using the methods described herein are nucleic acid templates, generally as part of complexes with polymerase molecules. Such nucleic acid templates can include any nucleic acid molecules known in the art and described herein. In some embodiments, the templates have lengths of about 50 to 600 nucleotides. In another embodiment, the nucleic acids are 300 to 600 or 200 to 20000 nucleotides in length. In yet another embodiment, the nucleic acid templates are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, 50-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 10000-30000, 12000-28000, 14000-26000, 16000-24000, 18000-22000, 19000-20000 nucleotides in length. In further embodiments, the nucleic acid templates are part of polymerase-template complexes. In yet further embodiments, the nucleic acid templates are themselves further hybridized to primers.

In further embodiments and in accordance with any of the above, the spike solution has a greater viscosity than the buffer into which it is placed. "Viscosity" as used herein refers to dynamic viscosity, the resistance of a fluid to shearing flow. The unit of viscosity in SI is the Poiseuille (PI) [1 PI=1 Pa*s] or the Poise (P) [1P=0.100 kg/ms. In general, the viscosity of the spike solution is no more than 10× that of the viscosity of water. In certain embodiments, the viscosity of the spike solution is no more than 8×, 6×, 4×, or 2× that of water. (Water has a viscosity of approximately 1 centipoise (cP).) In further embodiments, the balance between the viscosity and density of the spike solution is such that the efficiency of the loading of spike solution (and the molecules that it contains) is increased over that of solutions that do not have that balance between viscosity and density. In further embodiments, the viscosity of the spike solution is about 1.5-10, 2-9, 2.5-8, 3-7, 3.5-6, 4-5 cP. In still further embodiments, the density of the spike solution is from about 1-5, 1.1-1.5, 1.2-2.0, 1.3-2.5, 1.4-3.0, 1.5-3.5, 1.6-4.0, 1.7-4.5, 1.8-5, 1.9-5.5, 2.0-6.0 g/cm³ and a viscosity of about 2-12, 3-11, 4-10, 5-9, 6-8 cP.

II.B. Methods Utilizing Immiscible Liquids

In some aspects, polymerase compositions are loaded onto a surface through the use of immiscible liquids. In such examples, the surface is covered by a nonaqueous solution (in one non-limiting example, mineral oil). Droplets of aqueous solution comprising polymerase molecules (and/or other molecules) are added to the nonaqueous solution such that the aqueous droplets sink through the non-aqueous solution to form a film over the surface. As discussed above for methods utilizing spike solutions, these methods utilizing immiscible liquids may load molecules to a surface that further includes a plurality of array regions, which may in turn comprise nanowells or nanopores. Nanowells may further comprise without limitation ZMWs. In certain embodiments, the plurality of array regions comprise hydrophilic surfaces.

In exemplary embodiments, the non-aqueous solution is a hydrophobic liquid, and in further embodiments that hydrophobic liquid comprises mineral oil.

In further embodiments, after the aqueous droplets (and the molecules they contain) are distributed to the surface, the nonaqueous solution is removed or diluted, leaving only the molecules loaded onto the surface bathed in the aqueous solution that has formed a film over that surface. In yet further embodiments, the non-aqueous solution is removed or diluted through one or more washes with an aqueous buffer.

In further embodiments, the aqueous solution has higher density than the non-aqueous solution. The density of the aqueous solution can be of any density that is higher than that of the nonaqueous solution. In some non-limiting embodiments, the density of the aqueous solution is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0× higher than the density of the nonaqueous solution. In further embodiments, the density of the aqueous solution is 0.5-3×, 0.6-2.5×, 0.8-2.0×, 1.0-1.5× higher than the density of the nonaqueous solution. In still further embodiments, the density of the aqueous solution is about 1-5, 1.1-1.5, 1.2-2.0, 1.3-2.5, 1.4-3.0, 1.5-3.5, 1.6-4.0, 1.7-4.5, 1.8-5, 1.9-5.5, 2.0-6.0 g/cm³.

In general, methods utilizing the above-described immiscible liquids distribute the molecules (such as polymerase compositions) contained in the aqueous solution at a faster rate than loading under conditions that do not include use of both an aqueous and non-aqueous solution. In further embodiments, the distributing occurs about 2-50 fold faster as compared to distributing by diffusion without the use of both an aqueous and non-aqueous solution. In further embodiments, the distributing with the immiscible liquids occurs at about a 5-45, 10-40, 15-35, 20-30 fold faster rate as compared to distributing without the use of both an aqueous and non-aqueous solution.

Similar to the methods described above for using spike solutions, methods utilizing immiscible liquids may also include a cleaning step prior to addition of the aqueous solution to the non-aqueous solution. The cleaning step is accomplished by applying particles to the spike solution to capture the molecules that need to be removed. In some embodiments, the particle is a paramagnetic particle that captures free polymerases and templates that are not part of polymerase-template complexes. In further embodiments, a plurality of oligonucleotides are attached to the paramagnetic particles, and in yet further embodiments, the molecules that are to be removed from the spike solution attach to the oligonucleotides, and the cleaning step further comprises removing the particles and their attached molecules. The attachment of the molecules to be removed can include binding, hybridization, or any other association with the oligonucleotides. As is described in further detail herein, the particles may comprise any number of oligonucleotides. In certain embodiments, the particles comprise about 50,000-100,000 or more oligonucleotides. In further embodiments, there is a spacer between the oligonucleotides and the particle, and that spacer may itself comprise a series of nucleotides or a polymeric linker. In yet further embodiments, the spacer is of sufficient length to stabilize the attachment of molecules to the oligonucleotides, particularly the attachment of free polymerases. Without being bound by mechanism, one possibility is that a length of about 10-15 basepairs between the particle and the oligonucleotide (which in certain examples includes a sequence complementary to a primer) produces an optimal structural distance for a free polymerase to attach to the oligonucleotide with more stability as compared to a situation in which a spacer is not used.

II.C. Methods Utilizing Evaporative Loading

In some examples, polymerase compositions are loaded onto a surface through an evaporative loading procedure in which the non-volatile components of a solution (e.g., polymerase enzymes and/or other associated molecules, such as nucleic acid templates, primers, nucleotides, divalent cations, and/or any other reagents that may be of in a polymerase-mediated reaction) are added to a surface in a buffer containing carbohydrate. The buffer is then dehydrated, concentrating the polymerase compositions to the surface while retaining activity of the polymerase enzyme. Of note is that the presence of carbohydrates in the buffer (including without limitation sucrose, dextrose, trehalose, and Ficoll) an important component to retaining activity of the polymerase compositions after dehydration.

In general, the inclusion of at least one type of carbohydrate to the solution containing the polymerase composition allows for concentration of the composition on a surface. The degree to which the polymerase composition can be concentrated can be tuned by the amount of carbohydrate added to the solution. Without being limited by mechanism, the polymerase composition will generally increase in concentration until the carbohydrate concentration exceeds its solubility limit, at which point polymerase compositions (which will in certain embodiments contain polymerase enzymes complexed with nucleic acid templates and also in some embodiments primers) will become trapped in the carbohydrate aggregate. The exceeding of the solubility limit of the carbohydrate can be accomplished by increasing the concentration of the carbohydrate, dehydrating the solution, and any combination thereof.

Carbohydrate additives can be included in the solution at any amount that stabilizes polymerase activity. In some embodiments, the solution containing the polymerase compositions contains carbohydrate additives in the amount of 1-75%, 5-70%, 10-65%, 15-60%, 20-55%, 25-50%, 30-45% weight/volume (w/v) of solution. In further embodiments, the solutions contain at least 10%, 20%, 30%, 40%, 50%, 60%, 70%, 80%, 90% additive. In particular embodiments, the additives are included to an amount that is close to or at the limit of their solubility.

Dehydration of the solution to concentrate the polymerase composition to the surface can be accomplished using any method known in the art, including without limitation application of vacuum, lyophilization, drying at room temperature, and drying with heat. As discussed above, the solution containing the polymerase composition will generally include a carbohydrate to help stabilize the activity of the polymerase composition upon dehydration. The solution may further (or in the alternative) contain additional reagents to enhance stabilization of the polymerase composition, including any reagents known in the art to stabilize nucleic acids, proteins and other molecules at ambient and high temperature, such as Tris-EDTA, DNAstable® Plus (Biomatrica), and GenTegra® DNA.

Figure 7:
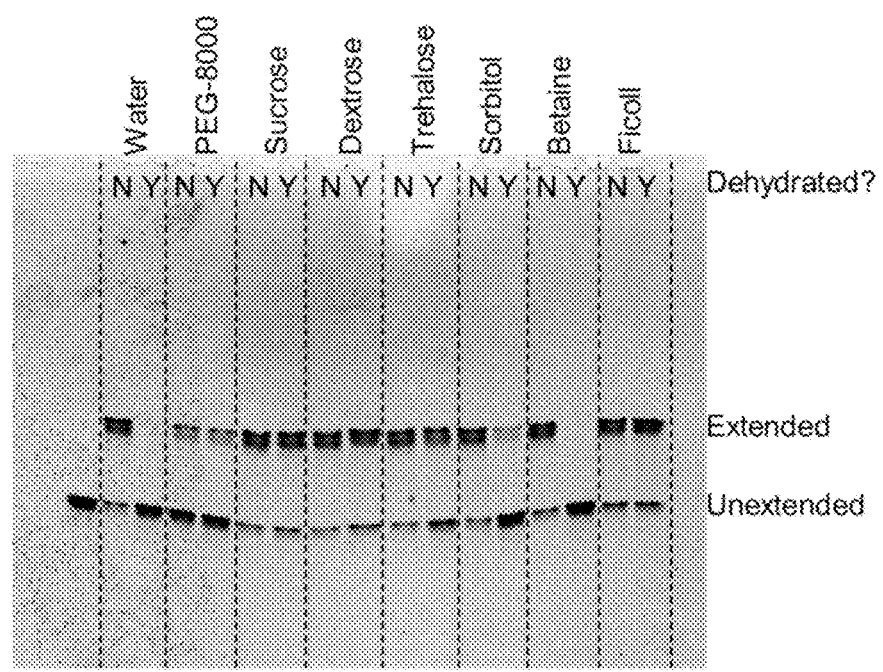
FIG. 7 shows the effect of carbohydrate additives on the stability of polymerase compositions after dehydration.

As shown in FIG. 7, complexes formed in the presence of betaine or 10% of the indicated additive were either dehydrated or not (see top line of figure). In the absence of additive (water) or the presence of betaine, the dehydrated sample was not able to extend the primer—however, the samples with carbohydrate additives maintained their activity after dehydration, (by maintained their activity is meant that the polymerases were able to extend the primer after being dehydrated and then rehydrated with an equivalent mass of solution such as deionized water). For example, the lanes for samples in which PEG-8000, sucrose, dextrose, trehalose, sorbitol or Ficoll were added showed activity after dehydration in FIG. 7.

III. Compositions

III.A. Particles for Cleaning Step

As discussed above, the methods disclosed herein include a step for removing unwanted molecules from the spike solution prior to using the spike solution for loading to the surface in accordance with any of the methods described herein. This cleaning step is generally accomplished using a particle. The terms "particle" and "bead" are used interchangeably herein and refer to any object that can be used to support a plurality of oligonucleotides for use in the cleaning steps described herein. Such particles and beads include without limitation latex beads, glass beads, polymeric beads, metal nanoparticles, magnetic particles, including magnetic nanoparticles, and avidin particles. The particles may further include without limitation inorganic materials, such as semiconductor nanoparticles, including e.g., II-V and II-VI core shell nanocrystals and the like. As will be appreciated, although particles can be spherical objects, any shape and size of can be used in accordance with the invention described herein. In some embodiments, the beads further comprise a polymeric coating on their surface.

In exemplary embodiments, the particles used in the cleaning steps described herein have a plurality of oligonucleotides attached to them. These oligonucleotides generally are capable of hybridizing, binding or otherwise attaching to molecules in the spike solution. The particles are designed such that polymerase enzymes, nucleic acid templates, and/or primers in any combination bind to, hybridize to, or otherwise attach to the oligonucleotides attached to the particles.

Figure 2:
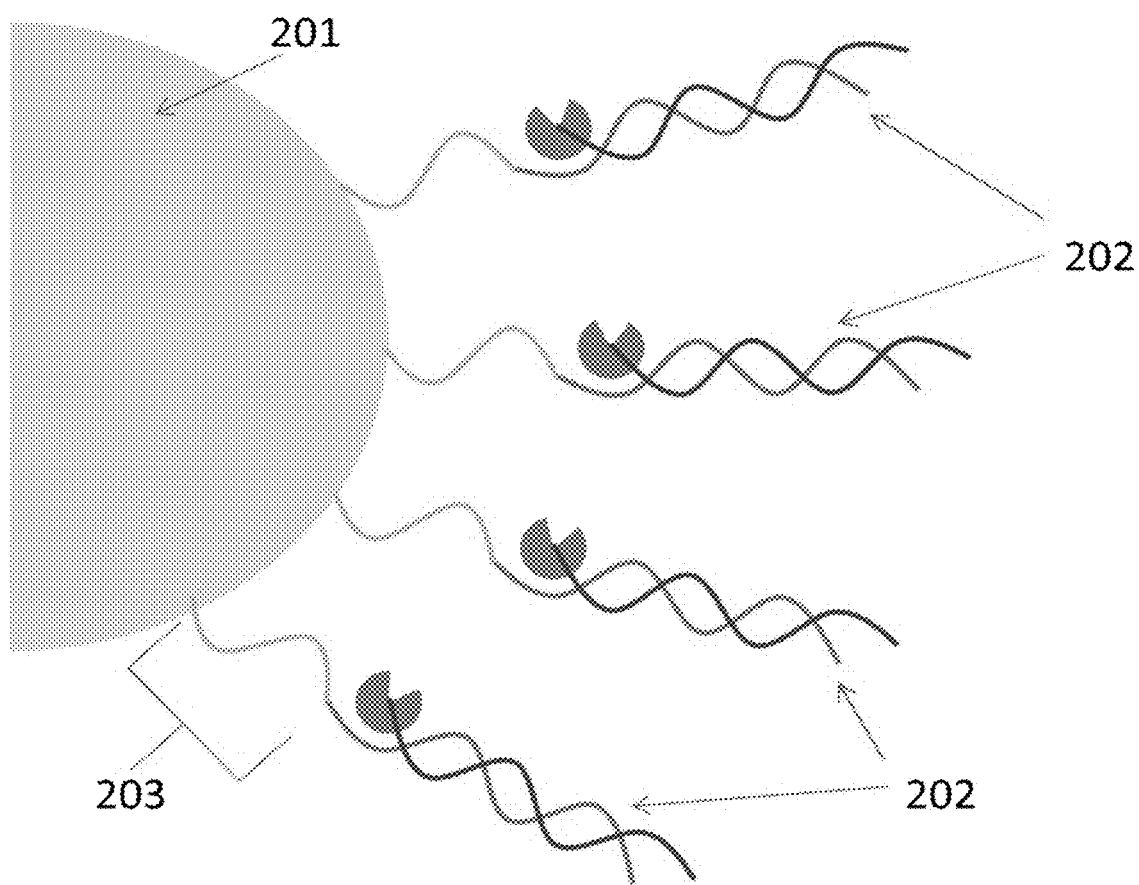
FIG. 2 is a schematic illustration of an embodiment of the invention.

One embodiment of particles encompassed by the present disclosure is shown in FIG. 2. In such an embodiment, the particle is a bead (201) that has attached to it a plurality of oligonucleotides (202). Polymerase enzymes, template nucleic acids, and primers that are not part of a complex are able to bind to or otherwise associate with the plurality of oligonucleotides on the bead and can then be removed from the spike solution by removing the particles using any methods known in the art and described herein.

In further embodiments, the plurality of oligonucleotides attached to the particles will further include a spacer (203). In general, the spacer is of sufficient length that association of polymerases with the oligonucleotides is stabilized as compared to situations in which the spacer is not present or is not of the proper length. The spacer may itself be in certain examples a series of nucleotides or a linker molecule. In examples in which the spacer is a series of nucleotides, the sequence of nucleotides is generally one that will not itself hybridize to a primer or template nucleic acid. Such a sequence produces a distance between the particle and the remainder of the oligonucleotide that stabilizes the association of polymerases as well as nucleic acid templates and primers to the plurality of oligonucleotides attached to the bead. In further examples in which the spacer is a series of nucleotides, the spacer generally has a length of about 10 to about 20 basepairs (bp). As will be appreciated, the particles can be designed to leave the spike solution enriched for whatever combination of molecules that is required—for example, the particles can be designed to associate primarily with free primers but not with as many free nucleic acid templates and/or polymerases. Such designs are generally accomplished through modifications of the attached oligonucleotides and spacers.

In some embodiments, the spacer is a linker. The term "linker" or "linker moiety" encompasses any moiety that is useful to connect the oligonucleotide to the particle. (e.g., a fluorescent dye molecule) to a nucleotide (e.g., a deoxynucleotide). In certain embodiments, a linker is a single covalent bond or a series of stable covalent bonds incorporating 1-40, e.g., 10-30 nonhydrogen atoms selected from the group consisting of C, N, O, S and P that covalently attach the oligonucleotides to the particle, in certain further embodiments through another moiety such as a chemically reactive group or a biological or non-biological component, e.g., a carrier molecule. Exemplary linkers include one or more linkage fragment, e.g., —C(O)NH—, —C(O)O—, —NH—, —S—, —O—, joining the particle to the linker and/or the linker to the oligonucleotide. In one embodiment, the linker is a member selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl. In one example, the linker moiety is selected from straight- and branched carbon-chains, optionally including at least one heteroatom (e.g., at least one functional group, such as ether, thioether, amide, sulfonamide, carbonate, carbamate, urea and thiourea), and optionally including at least one aromatic, heteroaromatic or non-aromatic ring structure (e.g., cycloalkyl, phenyl).

In specific embodiments, the particle used in cleaning steps of methods described herein is a spherical bead. In further embodiments, the particle is a paramagnetic particle. In yet further embodiments, the particle comprises a polymer layer.

As will be appreciated, particles of use in the cleaning steps of the methods described herein can be of any size that is useful for those cleaning steps. In specific embodiments, the particles are beads of about 100 to about 750 nm in diameter. In further embodiments, the particles are beads of about 150-650, 175-600, 200-550, 250-500, 300-450 nm in diameter. In yet further embodiments, the particle is a bead of about 100, 200, 300, 400, 500, 600, 700, 800, 900 nm in diameter. In still further embodiments, the particle is a bead of at least 50, 100, 150, 200, 250, 300, 350, 400, 450, 500, 550, 600 nm in diameter.

As discussed above, particles of use in the methods described herein may contain a plurality of oligonucleotides on their surface along with spacers. In certain embodiments, such spacers are located between the particle and the oligonucleotide sequence. In further embodiments, the oligonucleotide comprises a sequence complementary to a primer (also referred to as a "primer binding sequence"), and the spacer is located between the particle and the primer binding sequence. In still further embodiments, the spacer itself comprises an oligonucleotide with a length of about 10-20, 11-19, 12-18, 13-17, 14-16 bp. In yet further embodiments, the spacer has a length of about 10, 11, 12, 13, 14, 15, 16, 17, 18, 19, 20, 21, 22, 23, 24, 25, 26, 27, 28, 29, 30 bp. In some embodiments, the spacer comprises a linker that is a member selected from the group consisting of: saccharide, amino acid, substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl.

In further embodiments and in accordance with any of the above, particles of use in the methods of the present disclosure comprise plurality of oligonucleotides. In still further embodiments, the particles comprise about 75,000 to about 150,000 oligonucleotides. In yet further embodiments, the particles comprise about 60,000-250,000; 65,000-225,000; 70,000-200,000; 75,000-175,000; 80,000-125,000; 90,000-100,000 oligonucleotides. In still further embodiments, the particles comprise at least about 50,000; 70,000; 90,000; 100,000; 110,000; 130,000; 150,000; 170,000; 190,000; 200,000; 210,000; 230,000; 250,000 oligonucleotides.

III.B. Template Molecules

Any of the methods and complexes described herein can include template nucleic acid molecules (also referred to herein as "template sequences"). In general, the template nucleic acid is a molecule for which the complimentary sequence could be synthesized in a polymerase reaction. As will be appreciated, template sequences can be of any length or structure. In some cases, the template nucleic acid is linear; in some cases, the template nucleic acid is circular. The template nucleic acid can be DNA, RNA, or can be a non-natural RNA analog or DNA analog. Any template nucleic acid that is suitable for replication by a polymerase enzyme can be used in the methods and systems described herein. As will be appreciated, a template nucleic acid that is suitable for replication by a polymerase enzyme may be loaded to a surface using any of the methods described herein, and such a template may be loaded as a free molecule or as part of a complex with other molecules or proteins, including for example as a complex with a polymerase enzyme or as a complex with a helicase.

In some embodiments, the template nucleic acids used in methods and compositions of the present disclosure comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (i.e. in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In further embodiments, nucleic acid molecules are obtained from a sample and fragmented for use in methods described herein as template nucleic acids. The fragments may be single or double stranded and may further be modified in accordance with any methods known in the art and described herein. Template nucleic acids may be generated by fragmenting source nucleic acids, such as genomic DNA, using any method known in the art. In one embodiment, shear forces during lysis and extraction of genomic DNA generate fragments in a desired range. Also encompassed by the present disclosure are methods of fragmentation utilizing restriction endonucleases.

As will be appreciated, the template nucleic acids may be generated from a source nucleic acid, such as genomic DNA, by fragmentation to produce fragments of a specific size. The target nucleic acids can be, for example, from about 10 to about 50,000 nucleotides in length, or from about 10 to about 20,000 nucleotides in length. In one embodiment, the fragments are 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length.

In some aspects, the nucleic acids used in the compositions and methods of the present disclosure comprise nucleoside polyphosphates (also referred to herein as "nucleotides" "nucleotide analogs" or "nucleoside polyphosphate analogs") that have a three or more phosphate groups. In exemplary embodiments, nucleotide analogs of use in methods described herein have at least 4, 5, 6, 7, 8, 9, 10, 11, 12, 13, 14, 15, 16, 17, 18, 19, 20, 21, 22, 23, 24, 25, 26, 27, 28, 29, 30 phosphate groups. In further exemplary embodiments, nucleotide analogs of use in methods of the present disclosure have about 4, 5, 6, 7, 8, 9, 10, 11, 12, 13, 14, 15, 16, 17, 18, 19, 20, 21, 22, 23, 24, 25, 26, 27, 28, 29, 30 phosphate groups. In still further exemplary embodiments, nucleotide analogs have from about 4-60, 5-55, 6-50, 7-45, 8-40, 9-35, 10-30, 11-25, 12-20, 13-15, 4-20, 4-12, 5-19, 6-18, 7-17, 8-16, 9-15, 10-14, 11-13 phosphate groups.

In some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, alternate functional circular constructs are also described in US Pat. App. Pub. No. 20090298075 the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In further aspects, the template nucleic acid used in the compositions of the present disclosure includes: a double stranded nucleic acid segment having a first and second end; a first hairpin oligonucleotide connecting each strand of the single template nucleic acid at the first end; a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In further embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In other embodiments, the capture adapter comprises at least one methoxy residue. In further embodiments, the capture adapter is complementary to an oligonucleotide attached to a bead, which can in further embodiments be a magnetic bead that can be used to enrich a population for template nucleic acids containing the capture adapter. In some embodiments in which the population of templates includes templates with different adapters or in which each template comprises a different adapter at each end, different beads can be used which contain oligonucleotides complementary to the different adapters. Thus, for templates with two different adapters, two different beads can be used. For populations containing a plurality of different adapters, a concomitant number of different types of beads can be used that are directed to those adapters. In other embodiments, the same bead can contain different oligonucleotides complementary to the different adapters in the population of templates, such that the same bead can capture different adapters (and their associated templates).

In still further embodiments, the first or second hairpin comprises a self-primed adapter sequence in which the primer is part of the adapter. In such embodiments, an additional oligonucleotide primer is not needed to allow a polymerase molecule to begin replicating the template.

In further embodiments and in accordance with any of the above, the nucleotide analogs of use in the present disclosure include 4 or more phosphate groups as discussed above and in addition include a terminal protecting group (also referred to herein as a "terminal blocking group") to protect the nucleotide analog from degradation until the nucleotide analog is incorporated and the polyphosphate chain is released, for example in one or more of the template-directed polymerization reactions in the stepwise and single molecule sequencing reactions discussed herein. The protecting group will in general be on the terminal phosphate of the polyphosphate chain of the nucleotide analog and can be any type of protecting group that prevent a hydrolysis reaction, such as a reaction by a phosphatase. In some embodiments, the nucleoside polyphosphate is protected by another nucleoside of the same base (e.g., a symmetric dinucleoside polyphosphate). In one non-limiting embodiment, the protecting group includes any group that takes the place of one or more of the oxygen atoms of the terminal phosphate group to prevent degradation. In further exemplary embodiments, the protecting group comprises a linker, an alkyl group (including without limitation a methyl, ethyl, propyl or butyl group), a dye, any other adduct (including without limitation a fluorophore, a carbohydrate, and an aromatic group) that is attached either to the P or an O in the terminal phosphate. In embodiments in which the protecting group is a linker, the linker can be any molecular structure, including without limitation organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In some embodiments, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes and in particular for all teachings related to linkers. The protecting groups may in further embodiments be alkyl, aryl, or ester linkers. The protecting groups may also be amino-alkyl linkers, e.g., amino-hexyl linkers. In some cases, the linkers can be rigid linkers such as disclosed in U.S. patent application Ser. No. 12/403,090, which is incorporated herein by reference in its entirety for all purposes and in particular for all teachings related to linkers.

In addition to the naturally occurring "nucleobases," adenine, cytosine, guanine and thymine (A, C, G, T), nucleic acid components of the compounds described herein optionally include modified bases. These components can also include modified sugars. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine. The dye of the present disclosure or another probe component can be attached to the modified base.

In further embodiments, the nucleotide analogs of the present disclosure may further include labels, such as fluorescent labeling groups. These labeling groups may also be such that the different types of nucleotide analogs may be distinguished from one another. In such embodiments, typically, each of the different types of nucleotide analogs will be labeled with a detectably different fluorescent labeling group, e.g., that possesses a detectably distinct fluorescent emission and/or excitation spectrum, such that it may be identified and distinguished from different nucleotides upon incorporation. For example, each of the different types of nucleotides, e.g., A, T, G and C, will be labeled with a fluorophore having a different emission spectrum. For certain embodiments, the nucleotide may include a fluorescent labeling group coupled to a portion of the nucleotide that is incorporated into the nascent nucleic acid strand being produced during synthesis, e.g., the nucleobase or sugar moiety. Nucleotide compositions having fluorophores coupled to these portions have been previously described (See, e.g., U.S. Pat. Nos. 5,476,928 and 4,711,955 to Ward et al.). As a result of the label group being coupled to the base or sugar portion of the nucleotide, upon incorporation, the nascent strand will include the labeling group. This labeling group may then remain or be removed, e.g., through the use of cleavable linkages joining the label to the nucleotide (See, e.g., U.S. Pat. No. 7,057,026). A variety of different fluorophore types, including both organic and inorganic fluorescent materials, have been described for biological applications and are likewise applicable in the methods and compositions described herein.

In further embodiments, nucleotide analogs may include nucleoside polyphosphates having the structure:

B-S-P-G wherein B is a natural or non-natural nucleobase, S is selected from a sugar moiety, an acyclic moiety or a carbocyclic moiety, P is a modified or unmodified polyphosphate, and G is a protecting group.

The base moiety, B, incorporated into the nucleotide analogs is generally selected from any of the natural or non-natural nucleobases or nucleobase analogs, including, e.g., purine or pyrimidine bases that are routinely found in nucleic acids and nucleic acid analogs, including adenine, thymine, guanine, cytidine, uracil, and in some cases, inosine. For purposes of the present description, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the compositions and methods of the present disclosure may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes and in particular for all teachings related to nucleobases and labeling nucleobases.

In some embodiments, for the nucleotide analogs used as discussed herein, the S group is generally a sugar moiety that provides a suitable backbone for a synthesizing nucleic acid strand. In it most preferred aspect, the sugar moiety is selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties may be incorporated as the "S" group in place of a sugar moiety, including, e.g., those described in published U.S. Patent Application No. 2003/0124576, incorporated herein by reference in its entirety for all purposes and in particular for all teachings related to sugar moieties of nucleotides and nucleotide analogs.

The P groups in the nucleotides are modified or unmodified polyphosphate groups. As discussed above, the number of phosphates in the polyphosphate can have 4, 5, 6, 7, 8, 9, 10, 11, 12, 13, 14, 15, 16, 17, 18, 19, 20, 21, 22, 23, 24, 25, 26, 27, 28, 29, 30 phosphate groups or more modified or unmodified phosphates. The unmodified phosphates have linearly linked —O—P(O)$_2$— units, for example a tetraphosphate, pentaphosphate, hexaphosphate, heptaphosphate, or octaphosphate. The P groups also include modified polyphosphates, for example by virtue of the inclusion of one or more phosphonate groups, effectively substituting a non-ester linkage in the phosphorous containing chain of the analog, with a more stable linkage. Examples of preferred linkages include, e.g., $CH_2$, methylene derivatives (e.g., substituted independently at one or more hydrogens with F, Cl, OH, $NH_2$, alkyl, alkenyl, alkynyl, etc.), $CCl_2$, $CF_2$, NH, S, $CH_2CH_2$, $C(OH)(CH_3)$, $C(NH_2)[(CH_2)_6CH_3]$, CH(NHR) (R is H or alkyl, alkenyl, alkynyl, aryl, $C(OH)[(CH_2)_nNH_2]$ (n is 2 or 3), and $CNH_2$. In particularly preferred aspects, methylene, amide or their derivatives are used as the linkages.

Other P groups of the presently disclosed invention have phosphate or modified phosphates in which one or more non-bridging oxygen is substituted, for example with S, or $BH_3$. In one aspect of the invention, one or more, two or more, three or more, or four or more non-bridging oxygen atoms in the P group has an S substituted for an O. The substitution of, sulfur atoms for oxygen can change the polymerase reaction kinetics such that a system having two slow steps can be selected. While not being bound by theory, it is believed that the properties of the nucleotide, such as the metal chelation properties, electronegativity, or steric properties are the nucleotide can be altered by the substitution of non-bridging oxygen for sulfur in P. In some cases, it is believed that the substitution of two or more non-bridging oxygen atoms with sulfur can affect the metal chelation properties so as to lead to a change in the kinetics of incorporation, which can be used to modulate the signals generated from the incorporation events discussed herein.

Suitable nucleotide analogs include analogs in which sulfur is substituted for one of the non-bridging oxygens. In some embodiments, the single sulfur substitution is made such that substantially only one stereoisomer is present. The nucleotide can have multiple phosphates in which one or more of the phosphates has a non-bridging sulfur in place of oxygen. The substituted phosphate in the nucleotide can be the R or the S stereoisomer.

G generally refers to a protecting group that is coupled to the terminal phosphorus atom via the $R_4$ (or $R_{10}$ or $R_{12}$) group. As discussed above, the protecting groups employed in the analogs of the presently disclosed invention may comprise any of a variety of molecules, including a linker, an alkyl group (including without limitation a methyl, ethyl, propyl or butyl group), any other adduct (including without limitation a fluorophore, a carbohydrate, and an aromatic group) or a label e.g., optical labels, e.g., labels that impart a detectable optical property to the analog, electrochemical labels, e.g., labels that impart a detectable electrical or electrochemical property to the analog, physical labels, e.g., labels that impart a different physical or spatial property to the analog, e.g., a mass tag or molecular volume tag. In some cases individual labels or combinations may be used that impart more than one of the aforementioned properties to the nucleotide analogs of the presently disclosed invention.

The protecting group may be directly coupled to the terminal phosphorus atom of the analog structure, in alternative aspects, it may additionally include a linker molecule to provide the coupling through, e.g., an alkylphosphonate linkage. A wide variety of linkers and linker chemistries are known in the art of synthetic chemistry may be employed in coupling the labeling group to the analogs. For example, such linkers may include organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes. Additionally, such linkers may be selectively cleavable linkers, e.g., photo- or chemically cleavable linkers or the like. The linkers can be alkyl, aryl, or ester linkers. The linkers can be, amino-alkyl linkers, e.g., amino-hexyl linkers. In some cases, the linkers can be rigid linkers such as disclosed in U.S. patent application Ser. No. 12/403,090.

The B, S, P, and G groups can be connected directly, or can be connected using an linking unit such as an —O—, —S—, —NH—, or —$CH_2$— unit.

III.C. Polymerases

The methods and compositions disclosed herein utilize polymerase enzymes (also referred to herein as "polymerases"). Any suitable polymerase enzyme can be used in the systems and methods disclosed herein. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions described herein are strand-displacing polymerases.

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases used in methods described herein. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 Polymerases For Nucleotide Analogue Incorporation by Hanzel et al. and WO 2008/051530 Polymerase Enzymes And Reagents For Enhanced Nucleic Acid Sequencing by Rank et al.), to alter branch fraction and translocation (e.g., U.S. patent application Ser. No. 12/584,481 filed Sep. 4, 2009, by Pranav Patel et al. entitled "Engineering Polymerases And Reaction Conditions For Modified Incorporation Properties"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 Active Surface Coupled Polymerases by Hanzel et al. and WO 2007/076057 Protein Engineering Strategies To Optimize Activity Of Surface Attached Proteins by Hanzel et al.). Any of these available polymerases can be modified in accordance with the methods known in the art to decrease branching fraction formation, improve stability of the closed polymerase-DNA complex, and/or alter reaction rate constants. In some cases, the polymerase is modified in order to more effectively incorporate nucleotide analogs, e.g. analogs having four or more phosphates in their polyphosphate chain, and/or nucleotide analogs having terminal groups to prevent phosphate cleavage by phosphatase enzymes. Enzymes mutated to more readily accept nucleotide analogs having such properties are described, for example in the applications described above and in US 20120034602—Recombinant Polymerases for Improved Single Molecule Sequencing; US 20100093555—Enzymes Resistant to Photodamage; US 20110189659—Generation of Modified Polymerases for Improved Accuracy in Single Molecule Sequencing; US 20100112645—Generation of Modified Polymerases for Improved Accuracy in Single Molecule Sequencing; US 2008/0108082—Polymerase enzymes and reagents for enhanced nucleic acid sequencing; and US 20110059505—Polymerases for Nucleotide Analogue Incorporation which are incorporated herein by reference in their entirety for all purposes.

Many polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. No. 12/924,701, filed Sep. 30, 2010; and Ser. No. 12/384,112, filed Mar. 30, 2009.

In further embodiments, the polymerase enzyme used in the methods described herein includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

The polymerase enzymes of use in the methods and compositions described herein generally require a primer. While in most cases an oligonucleotide primer is used, in some cases a protein such as a terminal protein can acts as a primer. Oligonucleotide primers are generally complementary to a portion of the template nucleic acid. The primers can comprise naturally occurring RNA or DNA oligonucleotides. The primers may also be synthetic analogs. The primers may have alternative backbones as described above. The primers may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. The primers can also be selected to influence the kinetics of the polymerase reaction through the use of length, nucleotide content, and/or any of the modifications discussed above.

IV. Applications: Sequencing

The methods, devices, and compositions of the presently disclosed invention are particularly useful for single molecule sequencing methods, and specifically single molecule sequencing by incorporation in real time, because the methods and compositions for the present disclosure provide a way to efficiently establish a high density array of reaction regions occupied polymerase compositions. As discussed above, the loading of the polymerase compositions into the array is accomplished more quickly and with lower concentrations of input sample than is generally required in typical loading methods that rely on diffusion. These methods thus reduce the time and resources required to establish the array for use in methods such as sequencing methods. In specific embodiments, the methods result in loading an array of reaction regions such that a single polymerase enzyme or a single polymerase enzyme complexed with a nucleic acid template and a primer occupy a plurality of the reaction regions, thus allowing for single molecule sequencing from those reaction regions.

In some aspects, the present disclosure includes methods of analyzing the sequence of template nucleic acids associated with the polymerase compositions discussed herein. In such aspects, the sequence analysis employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in embodiments utilizing sequence by synthesis processes, individual nucleotides or nucleotide analogs are identified iteratively as they are added to the growing primer extension product.

For sequencing processes that rely upon monitoring of the incorporation of nucleotides into growing nascent strands being synthesized by the complex, the progress of the reaction through these steps can be of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product. By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

In further aspects, the methods of the present disclosure include steps from any single molecule sequencing methods known in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

In further embodiments, methods of single molecule sequencing known in the art include detecting individual nucleotides as they are incorporated into a primed template, i.e., sequencing by synthesis. Such methods often utilize exonucleases to sequentially release individual fluorescently labeled bases as a second step after DNA polymerase has formed a complete complementary strand. See Goodwin et al., "Application of Single Molecule Detection to DNA Sequencing," Nucleos. Nucleot. 16: 543-550 (1997).

In general, for sequencing methods utilizing compositions of the present disclosure, individual polymerase compositions are provided within separate discrete regions of a support. For example, in some cases, individual complexes may be provided within individual confinement structures, including nanoscale structures such as nanowells. In further examples, zero-mode waveguide cores or any of the reaction regions discussed above in the stepwise sequencing section serve as the reaction regions for sequencing methods utilizing compositions of the present disclosure. Examples of waveguides and processes for immobilizing individual complexes therein are described in, e.g., Published International Patent Application No. WO 2007/123763, the full disclosure of which is incorporated herein by reference in its entirety for all purposes and in particular for all teachings related to providing individual complexes into individual confinement structures. In some cases the complexes can be provided onto or proximal to structures or regions that allow for electronic single molecule sequencing. Such structures can include nanoscale electronic structures such as electrodes, capacitors, or field effect transducers (nanoFETs). NanoFETs include those having carbon nanotube gates. Such structures and their use for single molecule sequencing are described, for example, in U.S. Patent Application Publication No. 2015/0065353 which is incorporated herein in its entirety for all purposes and in particular for all teachings related to structures for use in single molecule sequencing.

The sequencing processes, e.g., using the substrates and compositions described herein, are generally exploited in the context of a fluorescence microscope system that is capable of illuminating the various complexes on the substrate, and obtaining detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the system, methods and compositions described herein. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purpose.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse that carries a distinguishable spectral profile or color.

In further embodiments, compositions described herein are utilized in sequencing methods utilizing nanopores. Such compositions that are loaded to the nanopores can include nucleic acid templates, helicases, exonucleases, polymerases, and any combination thereof. As will be appreciated, helicases and exonucleases as well as polymerases can be used in nanopore sequencing and loaded to nanopores using any of the methods described herein. Methods of nanopore sequencing are known in the art and disclosed for example in US Published App. Nos. 2013/0327644 and 2014/0051068, which are hereby incorporated by reference for all purposes and in particular for all teachings, written description, figures and figure legends related to nanopore sequencing.

The methods described herein can further include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the presently disclosed invention can range from personal computers such as PC or Macintosh® type computers running Intel Pentium or DuoCore processors, to workstations, laboratory equipment, or high speed servers, running UNIX, LINUX, Windows®, or other systems. Logic processing may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the presently disclosed invention may generally be programmed in a variety of programming languages including, e.g., Matlab, C, C++, C#, NET, Visual Basic, Python, JAVA, CGI, and the like.

In some cases, the compositions, methods, and systems of the present disclosure can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof which are incorporated herein by reference in their entirety for all purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents that provide the catalytic and non-catalytic metal co-factors employed in the processes described herein. The kits will also optionally include other components for carrying out sequencing applications in accordance with those methods described herein. In particular, such kits may include ZMW array substrates for use in observing individual reaction complexes as described herein.

In further exemplary embodiments, kits of the present disclosure include (alone, or in any combination with the above described components of kits) components for use in the loading methods described herein. Such components may include in any combination one or more of the following: standard buffer for covering the surface, high density loading solution, polymerase enzymes, nucleic acid templates, primer sequences, particles for cleaning the high density loading solution, and any other composition described herein associated with loading polymerase compositions to a surface and/or conducting a sequencing reaction.

In addition to the various components set forth above, the kits will typically include instructions for combining the various components in the amounts and/or ratios set forth herein, to carry out the desired processes, as also described or referenced herein, e.g., for performing sequence by incorporation reactions and/or loading methods.

In one aspect, the present disclosure provides methods and compositions for sequencing in which the sequence of a plurality of template nucleic acids is identified. "Primed nucleic acids" as discussed herein refer to nucleic acids that are in a condition to be replicated and/or extended in a template-directed manner, including without limitation nucleic acids hybridized to a primer that can be extended through the action of a polymerase as well as double stranded nucleic acids comprising a gap or a nick from which sequence-dependent replication can occur.

Different types of nucleotide analogs of use in the present disclosure may in some embodiments each have a different number of phosphate groups in the polyphosphate chain, such that each type may be identified from each other type upon incorporation. For example, the different types of nucleotide analogs may each correspond to a nucleobase independently selected from A, G, C, or T (or to one or more modified nucleobases), and each type may be distinguished from the other types based on characteristics such as the signal generated when the nucleotide analog is incorporated during a polymerase reaction. For example, each type of nucleotide analog can in some embodiments have a different number of phosphate groups in the polyphosphate chain, such that, upon incorporation of a particular nucleotide analog type during a polymerization reaction, the signal associated with the resultant cleavage of the phosphate bonds of the polyphosphate chain will identify the incorporated nucleotide analog as having a nucleobase A, C, G, or T. In further embodiments, sequencing reactions discussed herein may utilize 1, 2, 3, 4, 5, 6, 7, 8, 9, 10, 11, 12 or more different types of nucleotide analogs, and in further exemplary embodiments each of the different types of nucleotide analogs has a different number of phosphate groups in their polyphosphate chains.

Although in general the sequencing methods described herein utilize one type of nucleoside polyphosphate for each round of incorporation and detection, it will be appreciated that such sequencing methods may also be conducted with multiple (1, 2, 3, 4, 5, 6, 7, 8, 9, 10, 11, 12 or more different types of nucleotide analogs) during each round of incorporation and detection. In further exemplary embodiments, each of the different types nucleotide analogs of use in the sequencing methods discussed herein have a number of phosphate groups independently selected from 3, 4, 5, 6, 7, 8, 9, 10, 11, 12, 13, 14, 15, 16, 17, 18, 19, 20, 21, 22, 23, 24, 25, 26, 27, 28, 29, or 30 phosphate groups.

In still further aspects, the exposing and detecting steps are repeated with a second, third and fourth type of nucleoside polyphosphates enough times to identify the sequence of the plurality of template nucleic acids V. Substrates and Surfaces Substrates of use in methods described herein are known in the art and discussed herein, and as will be appreciated, any of the substrates discussed herein can be used in any combination for any embodiment of a sequencing reaction. In exemplary embodiments, methods of sequencing utilize substrates that include one or more reaction regions (also referred to herein as "reaction chambers" and "array regions") arranged in the form of an array on an inert substrate material, also referred to herein as a "solid support" or "surface", that allows for combination of the reactants in a sequencing reaction in a defined space and for detection of the sequencing reaction event. A reaction region can be a localized area on the substrate material that facilitates interaction of reactants, e.g., in a nucleic acid sequencing reaction. A reaction region may in certain embodiments be a nanoscale well (also referred to herein as a nanowell), and in further embodiments the nanowell is a ZMW. As discussed herein, the sequencing reactions contemplated by the present disclosure can in some embodiments occur on numerous individual nucleic acid samples in tandem, in particular simultaneously sequencing numerous nucleic acid samples derived from genomic and chromosomal DNA. The apparatus can therefore include an array having a sufficient number of array regions/reaction regions to carry out such numerous individual sequencing reactions. In one embodiment, the array comprises at least 1,000 reaction regions. In another embodiment, the array comprises greater than 400,000 reaction regions, preferably between 400,000 and 20,000,000 reaction regions. In a more preferred embodiment, the array comprises between 1,000,000 and 16,000,000 reaction regions.

The reaction regions on the array may take the form of a cavity or well in the substrate material, having a width and depth, into which reactants can be deposited. One or more of the reactants typically are bound to the substrate material in the reaction region and the remainder of the reactants are in a medium which facilitates the reaction and which flows through the reaction region. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have a planar bottom or a concave bottom. The reaction regions can be spaced between 5 μm and 200 μm apart. Spacing is determined by measuring the center-to-center distance between two adjacent reaction regions. Typically, the reaction regions can be spaced between 1 μm and 200 μm apart, 5 μm and 20 μm apart, 15 μm and 50 μm apart, 10 μm and 150 μm apart, preferably between 50 μm and 100 μm apart. In one embodiment, the reaction regions have a width in one dimension of between 0.3 μm and 100 μm. The reaction regions can have a width in one dimension of between 0.3 μm and 20 μm, preferably between 5 μm and 20 μm, between 0.3 μm and 10 μm, and most preferably about 6 μm. In some embodiments, the reaction regions have a width in one dimension of between 100-500 nm, 200-400, 100-300, 150-200 nm. In another embodiment, the reaction regions have a width of between 20 μm and 70 μm. Ultimately, the width of the chamber may be dependent on whether the nucleic acid samples require amplification. If no amplification is necessary, then smaller, e.g., 0.3 μm is preferred. If amplification is necessary, then larger, e.g., 6 μm is preferred. The depth of the reaction regions are preferably between 10 μm and 100 μm. Alternatively, the reaction regions may have a depth that is between 0.25 and 5 times the width in one dimension of the reaction region or, in another embodiment, between 0.3 and 1 times the width in one dimension of the reaction region.

Any material can be used as the solid support material, as long as the surface allows for stable attachment of the primers and detection of nucleic acid sequences. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

Suitable substrates include chips having arrays of nanoscale wells or zero mode waveguides. Such substrates are described, for example in U.S. patent application Ser. Nos. 10/259,268, 14/187,198, 14/107,730, 13/920,037, and U.S. Pat. Nos. 8,994,946, 8,906,670, 8,993,307, 8,802,600, and 7,302,146, which are incorporated herein by reference in their entirety for all purposes and in particular for all teachings related to substrates.

EXAMPLES

Example 1: Comparison of Density Loading to Diffusion Loading

Figure 3:
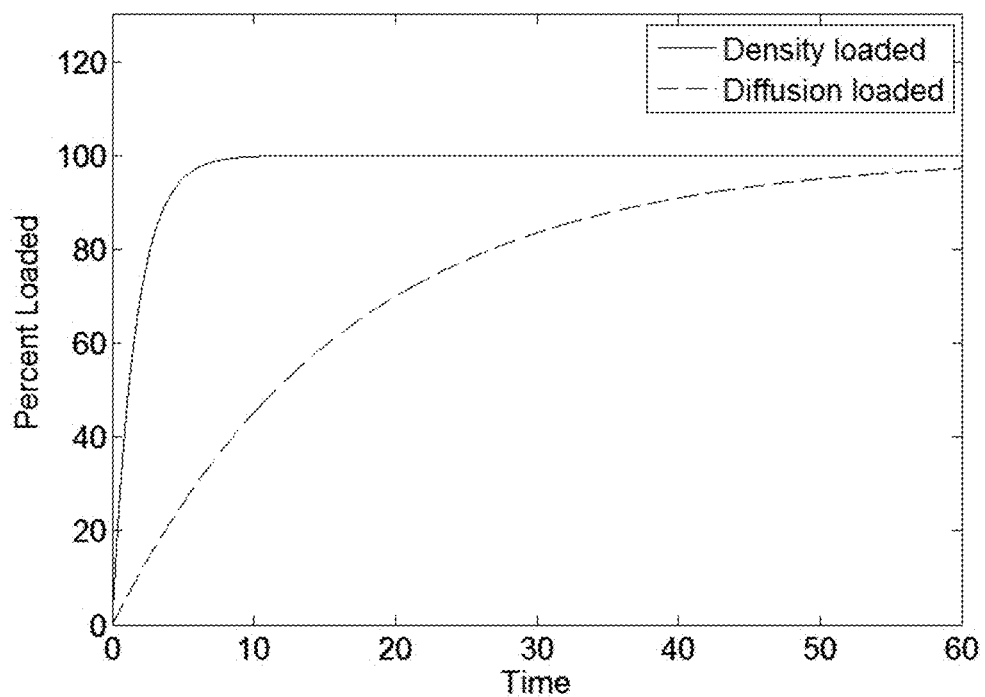
FIG. 3 shows data comparing the rate of loading under typical diffusion conditions to loading using high density solutions of the invention.

FIG. 3 shows that the fraction of ZMWs loaded with a polymerase-DNA complex as a function of time with density loading is significantly enhanced as compared to normal diffusion loading. For the density loading conditions, 4 uL of DNA-polymerase complex at 50 picomolar concentration was slowly pipetted through a layer of 36 uL of buffer containing 100 mM potassium acetate and 50 mM Tris-HCl buffered at pH=8. In the diffusion conditions 40 uL of DNA-polymerase complex at 5 picomolar concentration was added directly to the ZMW containing chip, so that the total amount of DNA-polymerase sample was the same between the two experiments. The plot in FIG. 3 shows that the density loading method had an approximately ten-fold enhancement in loading rate compared to the same amount of sample loaded with normal diffusion loading.

Figure 4:
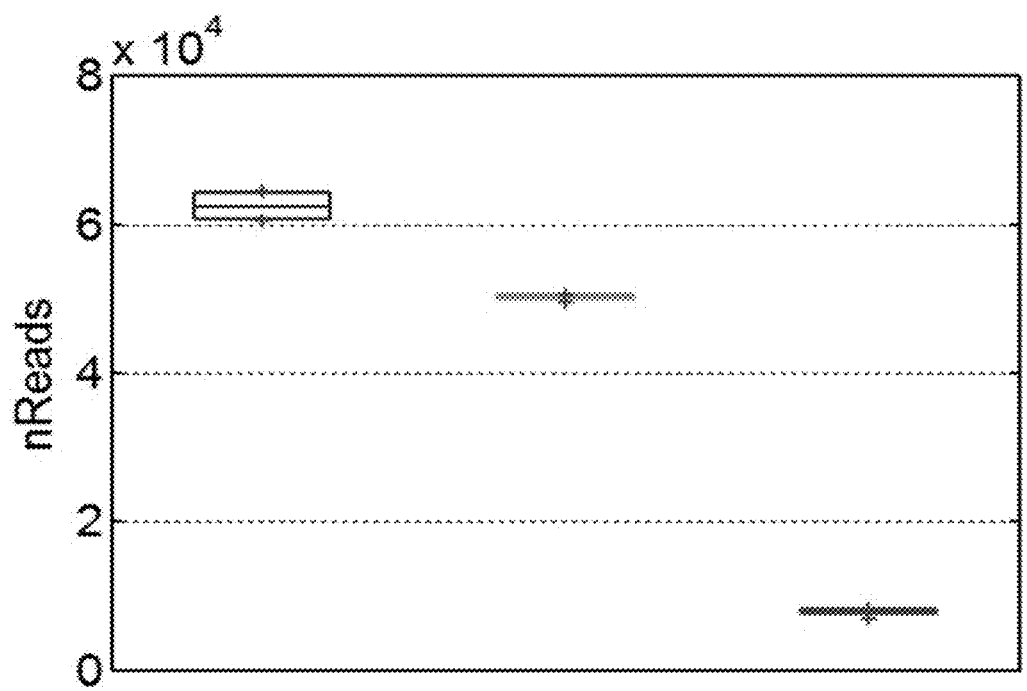
FIG. 4 shows data comparing the rate of loading under typical diffusion conditions to loading using high density solutions (spike) of the invention.

As shown in the plot in FIG. 4, diffusion loading (rightmost data point) had the lowest number of sequence reads (the indication of appropriate loading to the surface), whereas both conditions using a spike solution of higher density (in these experiments the spike solution contained Ficoll as indicated) showed higher numbers of sequence reads. Interestingly, for the same concentration of Ficoll, the lower volume spike solution showed a greater enhancement of loading. The data in FIG. 4 represent an N=4.

Example 2: Enhancement of Density Loading

Figure 5:
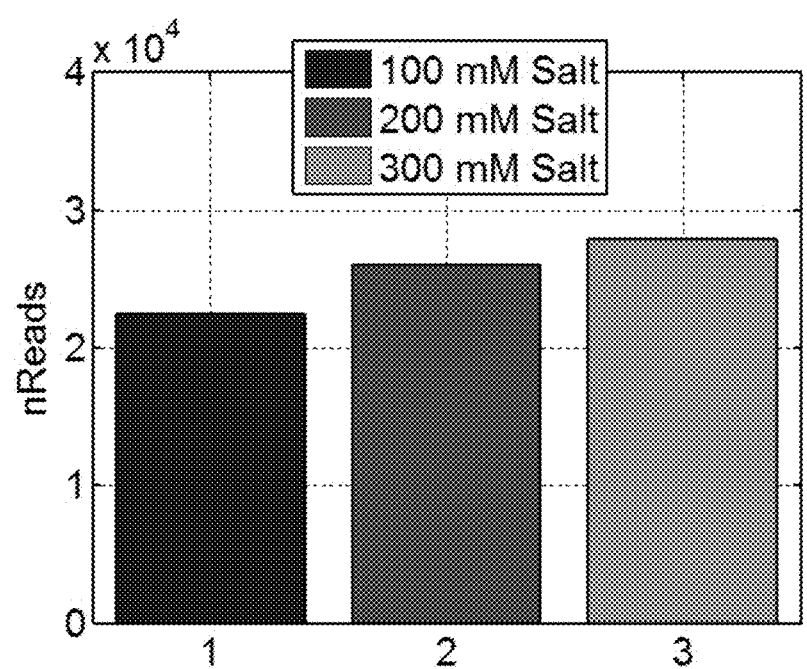
FIG. 5 shows the enhancement of both high density loading by increasing concentrations of salt (potassium acetate). The salt concentrations are 100 mM, 200 mM, and 300 mM from left to right.

FIG. 5 shows that increasing the salt (potassium acetate) concentration enhances density loading. The left-most bar is data in which the loading was conducted in the presence of 100 mM salt, the middle is in 200 mM salt, and the right-most bar is data in 300 mM salt. As shown in FIG. 5, increasing the salt concentration enhanced the efficiency of loading. The data in this figure was obtained with 0.5 fmoles of an 11 kb template using a 2 µL spike solution for loading into a standard buffer.

Example 3: Cleaning Step can Reduce Insertion Rate Errors

Figure 6:
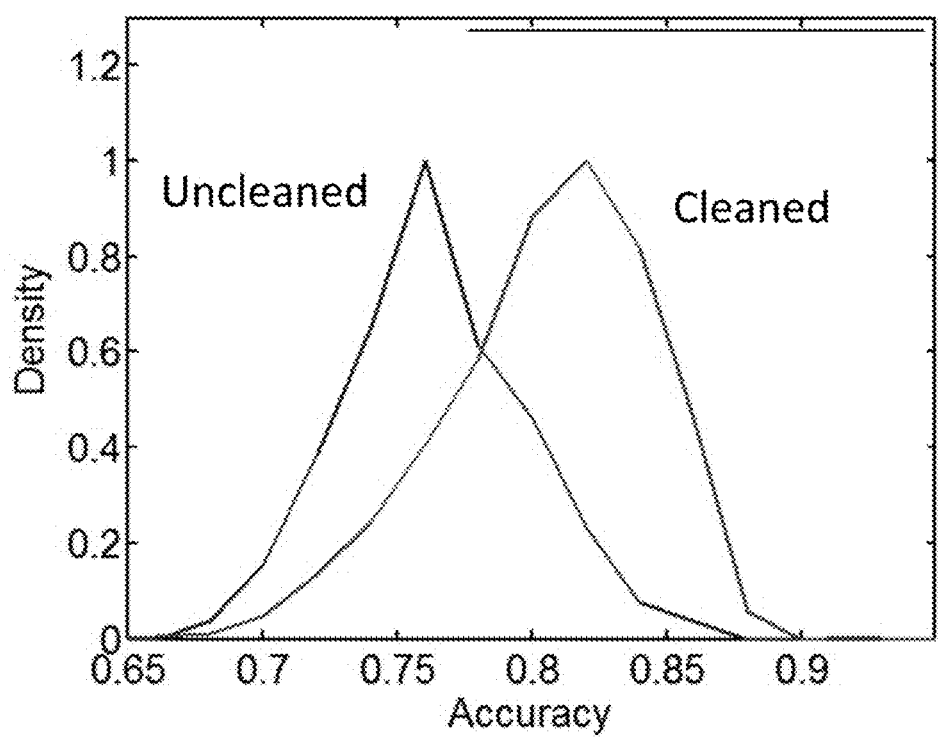
FIG. 6 shows the enhancement of accuracy for spike solutions that have undergone a cleaning step as compared to solutions that are not cleaned.

Including a cleaning step of the spike solution to remove polymerases and primers that are not part of complexes prior to loading can improve accuracy and reduce insertion rate errors, as shown in FIG. 6.

The cleaning step was part of the sample preparation process. The sample preparation process included the steps of shearing genomic DNA, ligating to adapters, and size selecting. The additional cleaning step included incubation with magnetic particles with oligonucleotides attached to their surface, where those oligonucleotides were structured to capture free polymerases and primers that were not part of complexes. The particles and their associated molecules were removed using a magnetic field and the remaining cleaned spike solution was loaded onto a surface containing ZMWs for sequencing.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method of distributing polymerase molecules into a plurality of array regions, the method comprising:
    (a) providing a surface comprising a plurality of array regions, wherein the plurality of array regions are bathed in a first solution comprising a buffer;
    (b) exposing the surface of step a) to a second solution comprising polymerase-template complexes, wherein the second solution has a higher density than the first solution, and wherein the second solution has a volume that is about 1% to about 20% of the volume of the first solution, such that the second solution sinks to the bottom of the array regions and forms a thin layer underlying the first solution,
    thereby distributing the polymerase-template complexes into the plurality of the array regions, wherein the distributing occurs at a faster rate as compared to distributing without a second solution with a higher density than the first solution.

2. The method of claim 1, wherein the second solution comprises a neutral and hydrophilic polysaccharide.

3. The method of claim 1, wherein the second solution comprises a highly branched, high-mass polysaccharide.

4. The method of claim 1, wherein the second solution comprises a volume excluding reagent.

5. The method of claim 1, wherein the second solution comprises an additive selected from the group consisting of dextran, aminodextran, dextrin, cluster dextrin, Ficoll, polyetheylene glycol, sucrose, DMSO, glycerol, and pullulan.

6. The method of claim 1, wherein the second solution comprises Ficoll.

7. The method of claim 1, wherein the distributing occurs at about a 2 to about a 25-fold faster rate as compared to distributing without the second solution.

8. The method of claim 1, wherein the distributing occurs at about a 5 to about a 20-fold faster rate as compared to distributing without the second solution.

9. The method of claim 1, wherein the distributing occurs at about a 10 to about a 15-fold faster rate as compared to distributing without the second solution.

10. The method of claim 1, wherein the distributing occurs at least 5 times faster as compared to distributing without the second solution.

11. The method of claim 1, wherein the distributing occurs at least 10 times faster as compared to distributing without the second solution.

12. The method of claim 1, wherein the distributing occurs at least 15 times faster as compared to distributing without the second solution.

13. The method of claim 1, wherein the volume of the second solution is about 5% to about 15% of the volume of the first solution.

14. The method of claim 1, wherein the volume of the second solution is about 10% of the volume of the first solution.

15. The method of claim 1, wherein prior to the exposing step (b), the second solution is cleaned to remove free polymerases that are not part of polymerase-template complexes.

16. The method of claim 15, wherein the second solution is cleaned by applying a paramagnetic particle to the second solution to capture free polymerases that are not part of polymerase-template complexes.

17. The method of claim 16, wherein the paramagnetic particle comprises a plurality of oligonucleotides, wherein the oligonucleotides comprise sequences complementary to a primer.

18. The method of claim 1, wherein the array regions comprise nanowells.

19. The method of claim 18, wherein the nanowells comprise zero mode waveguides (ZMWs).

20. The method of claim 1, wherein the distributing is complete in about 1-3 hours.

21. The method of claim 1, wherein the template of the polymerase template complexes comprises at least about 10-20 kilobasepairs (kbp) in length.

22. The method of claim 1, wherein the template of the polymerase template complexes comprises at least about 10 kbp in length.

23. The method of claim 1, wherein the template comprises:
   (i) a double stranded nucleic acid segment having a first and second end;
   (ii) a first hairpin oligonucleotide connecting each strand of the single template nucleic acid at the first end;
   (iii) a second hairpin oligonucleotide connecting each strand of the single template nucleic acid at the second end.

24. The method of claim 23, wherein the first hairpin oligonucleotide has an identical sequence to the second hairpin oligonucleotide.

25. The method of claim 23, wherein the first hairpin oligonucleotide comprises a primer binding site, and the second hairpin oligonucleotide comprises a capture adapter.

26. The method of claim 1, wherein the templates of the polymerase-template complexes are further hybridized to primers.

27. The method of claim 1, wherein subsequent to the distributing, the polymerase-template complexes are immobilized in the array regions.

28. The method of claim 1, wherein the second solution has greater viscosity than the first solution.

29. The method of claim 1, wherein the second solution has a density of about 1.1 to about 1.5 $g/cm^3$ and a viscosity of about 1.5-5 cP.

\* \* \* \* \*